(12) United States Patent
Tsuchiya

(10) Patent No.: US 7,250,257 B2
(45) Date of Patent: Jul. 31, 2007

(54) METHOD OF DETECTING MISMATCHING REGIONS

(75) Inventor: Toru Tsuchiya, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 345 days.

(21) Appl. No.: 10/953,418

(22) Filed: Sep. 30, 2004

(65) Prior Publication Data

US 2005/0130200 A1 Jun. 16, 2005

(30) Foreign Application Priority Data

Sep. 30, 2003 (JP) ............................. 2003-339713

(51) Int. Cl.
 C12Q 1/68 (2006.01)
 C07H 21/02 (2006.01)
 C07H 21/04 (2006.01)

(52) U.S. Cl. .................... 435/6; 536/23.1; 536/24.3

(58) Field of Classification Search .............. 435/6; 536/23.1, 24.3
See application file for complete search history.

(56) References Cited

U.S. PATENT DOCUMENTS

| | | | | |
|---|---|---|---|---|
| 5,391,480 A * | 2/1995 | Davis et al. | .................... | 435/6 |
| 5,753,439 A * | 5/1998 | Smith et al. | .................... | 435/6 |
| 5,873,941 A * | 2/1999 | Milliman | .................... | 118/419 |
| 5,919,623 A * | 7/1999 | Taylor | .................... | 435/6 |
| 5,958,692 A * | 9/1999 | Cotton et al. | .................... | 435/6 |
| 6,093,370 A | 7/2000 | Yasuda et al. | | |
| 6,340,566 B1 * | 1/2002 | McCutchen-Maloney | ...... | 435/6 |
| 6,403,309 B1 * | 6/2002 | Iris et al. | .................... | 435/6 |
| 6,900,013 B1 * | 5/2005 | Wang et al. | .................... | 435/6 |
| 2002/0016009 A1 | 2/2002 | Ogura | | |
| 2002/0048760 A1 * | 4/2002 | Drmanac et al. | ............... | 435/6 |
| 2002/0164778 A1 | 11/2002 | Kajiyama et al. | | |
| 2004/0048301 A1 * | 3/2004 | Sood et al. | .................... | 435/6 |
| 2004/0072247 A1 * | 4/2004 | Pfistershammer | ........... | 435/7.1 |
| 2004/0101891 A1 * | 5/2004 | Rigler et al. | .................... | 435/6 |
| 2004/0121344 A1 * | 6/2004 | Takarada et al. | ............... | 435/6 |
| 2006/0063191 A1 * | 3/2006 | Sutherland | .................... | 435/6 |

OTHER PUBLICATIONS

Till et al. Mismatch cleavage by single-strand specific nucleases. Nucleic Acids Research 32(8) : 2632-2641 (2004).*
Lyamichev et al., Polymorphism identification and quantitative detection of genomic DNA by invasive cleavage of oligonucleotide probes. Nature Biotechnology 17 : 292-296 (1999).*
Latif et al., Fluorescence polarization in homogeneous nucleic acid analysis II : 5'-nuclease assay. Genome Research 11:436-440 (2001).*
Mein et al., Evaluation of single nucleotide polymorphism typing with invader on PCR amplicons and its automation. Genome Research 10 :330-343 (2000).*
Hsu et al., Genotyping Single-Nucleotide polymorphisms by the invader assay with dual-color fluorescence polarization detection. Clinical Chemisty 47(8) :1373-1377 (2001).*

* cited by examiner

*Primary Examiner*—Ethan Whisenant
(74) *Attorney, Agent, or Firm*—Sughrue Mion, PLLC

(57) ABSTRACT

A labeled polynucleotide is subjected to hybridization with oligonucleotide probes fixed respectively to regions on a supporting material. With a first restriction enzyme, a single-stranded moiety of the labeled polynucleotide having failed to form a double strand with each probe is separated from a double strand having been formed by the labeled polynucleotide and each probe. First detection data is obtained from each region. A mismatching moiety, at which the labeled polynucleotide and a certain probe have undergone a mismatch binding, is separated with a second restriction enzyme, and second detection data is obtained from each region. The region to which the mismatch polynucleotide was bound is specified in accordance with results of a comparison between the first detection data and the second detection data.

5 Claims, 1 Drawing Sheet

EXONULEASE VII

FIRST DETECTION

S1 NUCLEASE

SECOND DETECTION

METHOD OF DETECTING MISMATCHING REGIONS

BACKGROUND OF THE INVENTION

1. Field of the Invention

This invention relates to a method of detecting a mismatching region, in which a mismatch binding has occurred, on a biochemical analysis micro array used for detection, analysis, or the like, of a specific sequence contained in a polynucleotide, such as a DNA.

2. Description of the Related Art

DNA micro arrays are expected to be applied to a wide range of fields of life science, such as monitoring of genetic expression, determination of base sequences of genes, analysis of gene polymorphism (SNP), analysis of gene amplification or deletion at cancered parts, classification of diseases, such as cancers, prediction of drug response characteristics, and searching of disease genes.

Principles of assay techniques utilizing DNA micro arrays are based upon detection of nucleic acids through hybridization. Specifically, various different probe DNA's are arrayed at a high density at a plurality of regions of a surface of a supporting material, such as glass, silicon, or a membrane filter, and secured to the regions of the surface of the supporting material. Thereafter, a target DNA (i.e., a DNA having been labeled with a labeling substance) is subjected to hybridization with the probe DNA's having been fixed to the regions of the surface of the supporting material. Signals obtained from the regions (spots) are then detected in the manner described below.

For example, in cases where the target DNA has been labeled with a radioactive labeling substance, a stimulable phosphor layer of a stimulable phosphor sheet is exposed to radiation radiated out from the radioactive labeling substance, which is contained selectively in the regions of the supporting material. Thereafter, the stimulable phosphor layer is exposed to stimulating rays, which cause the stimulable phosphor layer to emit light in proportion to the amount of energy stored on the stimulable phosphor layer during the exposure of the stimulable phosphor layer to the radiation. The light emitted by the stimulable phosphor layer is detected photoelectrically. In this manner, the target DNA having been specifically bound to at least one of the probe DNA'S, which have been fixed to the regions of the surface of the supporting material, is detected.

In cases where the target DNA has been labeled with a fluorescent labeling substance, excitation light is irradiated to the regions of the supporting material, and the fluorescent labeling substance, which is contained selectively in the regions of the supporting material, is excited by the excitation light to produce fluorescence. The thus produced fluorescence is detected photoelectrically.

In cases where the target DNA has been labeled with a chemical luminescent labeling substance capable of producing the chemical luminescence when being brought into contact with a chemical luminescence substrate, the chemical luminescent labeling substance, which is contained selectively in the regions of the supporting material, is brought into contact with the chemical luminescence substrate. Also, the chemical luminescence produced by the chemical luminescent labeling substance is detected photoelectrically. (The aforesaid assay techniques are described in, for example, U.S. Patent Laid-Open No. 20020016009.)

The DNA micro arrays may be classified into two groups in accordance with the kinds of the DNA's, which are arrayed, and processes for producing the DNA micro arrays. One of the two groups is an oligonucleotide array produced with a process, wherein a light blocking plate referred to as a mask is overlaid on a silicon base plate, the silicon base plate is exposed to light via the mask by the utilization of photo-lithography, which is an exposure technique for semiconductors, the operation for exposing the silicon base plate to light via the mask is iterated, and DNA molecules are thereby superposed one by one on the base plate. (The oligonucleotide array produced with the process described above will hereinbelow be referred to simply as the oligonucleotide array.) The other group is a cDNA micro array produced with a process, wherein cDNA's having been subjected to PCR amplification previously are spotted onto slide glass by use of a thin pin, an ink jet technique, or the like.

Conditions (such as a temperature and a salt concentration) optimum for the hybridization may vary for the different kinds of the probe DNA's having been fixed respectively to the regions. However, it is not always possible to perform the reaction under the conditions optimum for each of the probe DNA's, which have been fixed respectively to the regions having been located at a high density. Therefore, ordinarily, the reaction is performed under the identical conditions with respect to all of the regions. Accordingly, it may often occur that a target DNA, which is not perfectly complementary to a certain probe DNA on the array and has a sequence similar to the perfectly complementary sequence, undergoes incorrect hybridization with the aforesaid certain probe DNA on the array. The incorrect hybridization described above is referred to as the mismatch binding. The target DNA, which has undergone the mismatch binding, causes noise to occur at the time of signal detection and adversely affects a detection accuracy.

In particular, the cDNA micro array is produced by directly subjecting the cDNA's, which have been isolated from cells of organisms, to the PCR amplification and fixed to the slide glass. The cDNA micro array is not produced by previously designing the probe DNA's so as not to undergo a mismatch bonding as in the cases of the oligonucleotide array. Therefore, the cDNA micro array has a high possibility that the probe DNA's on the cDNA micro array will under go the mismatch binding. Accordingly, in the cases of the cDNA micro array, the mismatch binding is suppressed through preparation of the probes located on the cDNA micro array. For such purposes, for example, sequences specific to a gene to be detected are selected, and oligo DNA's having been synthesized in accordance with the selected sequences are used as the probes.

However, in both the cases of the oligonucleotide array and the synthetic oligo array, it is not always possible to design such that the mismatch binding does not occur. Particularly, in cases where analysis is to be made with respect to a long gene, such as a cDNA, it is almost impossible to design such that the mismatch binding does not occur.

Attempts have been made to solve the problems with regard to the mismatch binding described above by, for example, finely adjusting the temperature or the pH value at the time of hybridization of a target DNA with probe DNA's having been fixed to an array. For example, a biochemical reaction detecting chip for the hybridization of a polynucleotide with oligonucleotide probes, with which biochemical reaction detecting chip the biochemical reaction is capable of being caused to occur at a temperature optimum for the hybridization at each of probe fixing surfaces, has been proposed in, for example, U.S. Patent Laid-Open No. 20020164778. The proposed biochemical reaction detecting chip is based upon characteristics concerning a melting out temperature (i.e., a Tm value) of a complementary strand binding of oligonucleotide probes. Specifically, under conditions of temperatures lower than the Tm value, background noise due to the mismatch binding increases. Also, under conditions of temperatures higher than the Tm value, it becomes difficult for the polynucleotide to undergo the binding with the probes. Therefore, with the proposed biochemical reaction detecting chip, a temperature, at which the polynucleotide is capable of undergoing the hybridization with a probe such that the mismatch binding does not occur, is adjusted at a value optimum for each of the probes.

Also, a technique for selectively separating and recovering a desired polynucleotide is proposed in, for example, U.S. Pat. No. 6,093,370. With the proposed technique for selectively separating and recovering a desired polynucleotide, oligonucleotide probes are fixed respectively to regions of a surface of a base plate, and polynucleotides are subjected to the hybridization with the oligonucleotide probes. Thereafter, only a specific region of the base plate is heated selectively, and only the polynucleotide, which has been complementarily bound to the probe, is separated from the probe.

However, with the technique for utilizing the biochemical reaction detecting chip proposed in U.S. Patent Laid-Open No. 20020164778, it is necessary that a plurality of islands are formed on the biochemical reaction detecting chip, and that the temperature adjustment is monitored finely for each of the islands. Also, in cases where the technique for selectively separating and recovering a desired polynucleotide, which is proposed in U.S. Pat. No. 6,093,370, is utilized, it is necessary that only the specific region of the base plate is heated selectively. Further, the Tm values of the probes, which are contained in the islands or the regions described above, must be set previously at approximately identical values. As described above, with each of the technique for utilizing the biochemical reaction detecting chip proposed in U.S. Patent Laid-Open No. 20020164778 and the technique for selectively separating and recovering a desired polynucleotide, which is proposed in U.S. Pat. No. 6,093,370, complicated operations must be performed, and it is necessary for a specific apparatus to be utilized. Furthermore, in order for the mismatch binding to be suppressed, fine adjustment for raising or lowering the salt concentration in a liquid subjected to reaction must be made, and considerable labor and time are thus required. In cases where the hybridization is performed through adjustment of the pH value, the same problems as those described above arise.

As described above, in order for the mismatch binding during the hybridization to be suppressed, complicated adjustments must be performed, and considerable labor and time are required. Also, new problems occur in that, depending upon the conditions for the suppression of the mismatch binding, perfect match binding, i.e. perfect complementary binding, is weakened.

If a region, at which a target DNA having under gone the mismatch binding is located, is capable of being specified, for example, the thus specified region will be capable of being eliminated at the time of data analysis, and the detection accuracy will thus be capable of being kept high.

SUMMARY OF THE INVENTION

The primary object of the present invention is to provide a method of detecting a mismatching region, wherein a region, at which a mismatch binding has occurred during hybridization, is capable of being detected, and data obtained from the thus detected region is capable of being eliminated at the time of data analysis.

The present invention provides a method of detecting a mismatching region, comprising the steps of:

i) subjecting a labeled polynucleotide, which has been labeled with a labeling substance, to hybridization with a plurality of oligonucleotide probes, which have been fixed respectively to a plurality of regions on a supporting material, ii) causing a first restriction enzyme to act upon a single-stranded moiety of the labeled polynucleotide, which moiety has failed to form a double strand with each of the plurality of the oligonucleotide probes having been respectively fixed to the plurality of the regions on the supporting material, the first restriction enzyme being capable of decomposing a single-stranded polynucleotide from a terminal of the labeled polynucleotide, the single-stranded moiety of the labeled polynucleotide being thereby separated from a double strand, which has been formed by the labeled polynucleotide and each of the oligonucleotide probes, iii) detecting a signal, which is obtained from the labeling substance of the labeled polynucleotide, with respect to each of the regions on the supporting material after the single-stranded moiety of the labeled polynucleotide has been separated from the double strand, which has been formed by the labeled polynucleotide and each of the oligonucleotide probes, first detection data being obtained from the signal detection, iv) causing a second restriction enzyme to act upon a mismatching moiety, at which the labeled polynucleotide and a certain oligonucleotide probe among the plurality of the oligonucleotide probes having been respectively fixed to the plurality of the regions on the supporting material have undergone a mismatch binding with each other, after the first detection data has been obtained, the second restriction enzyme being capable of cutting off the mismatching moiety, the mismatching moiety, at which the labeled polynucleotide and the certain oligonucleotide probe have undergone the mismatch binding with each other, being thereby separated from a region on the supporting material, to which region the mismatch polynucleotide has been bound, v) detecting a signal, which is obtained from the labeling substance of the labeled polynucleotide, with respect to each of the regions on the supporting material after the mismatching moiety has been separated from the region on the supporting material, to which region the certain oligonucleotide probe has been fixed, second detection data being obtained from the signal detection, vi) making a comparison between the first detection data and the second detection data, and vii) specifying the region on the supporting material, to which region the mismatch polynucleotide was bound, in accordance with results of the comparison.

In the method of detecting a mismatching region in accordance with the present invention, the oligonucleotide probes are formed from nucleotides, which have approximately identical lengths, with respect to all of the regions on the supporting material.

The method of detecting a mismatching region in accordance with the present invention should preferably be modified such that the first restriction enzyme is exonuclease VII.

Also, the method of detecting a mismatching region in accordance with the present invention should preferably be modified such that the second restriction enzyme is at least either one of S1 nuclease and mung bean nuclease.

With the method of detecting a mismatching region in accordance with the present invention, after the labeled polynucleotide, which has been labeled with the labeling substance, has been subjected to the hybridization with the plurality of the oligonucleotide probes, which have been fixed respectively to the plurality of regions on the supporting material, the first restriction enzyme is caused to act upon the single-stranded moiety of the labeled polynucleotide, which moiety has failed to form the double strand with each of the plurality of the oligonucleotide probes having been respectively fixed to the plurality of the regions on the supporting material. The first restriction enzyme is capable of decomposing the single-stranded polynucleotide from the terminal of the labeled polynucleotide. The single-stranded moiety of the labeled polynucleotide is thereby separated from the double strand, which has been formed by the labeled polynucleotide and each of the oligonucleotide probes. Thereafter, the signal, which is obtained from the labeling substance of the labeled polynucleotide, is detected with respect to each of the regions on the supporting material, and the first detection data is obtained from the signal detection. After the first detection data has been obtained, the second restriction enzyme is caused to act upon the mismatching moiety, at which the labeled polynucleotide and the certain oligonucleotide probe among the plurality of the oligonucleotide probes having been respectively fixed to the plurality of the regions on the supporting material have undergone the mismatch binding with each other. The second restriction enzyme is capable of cutting off the mismatching moiety. The mismatching moiety, at which the labeled polynucleotide and the certain oligonucleotide probe have undergone the mismatch binding with each other, is thereby separated from the region on the supporting material, to which region the mismatch polynucleotide has been bound. Thereafter, the signal, which is obtained from the labeling substance of the labeled polynucleotide, is detected with respect to each of the regions on the supporting material, and the second detection data is obtained from the signal detection. The first detection data and the second detection data are then compared with each other. Therefore, with the method of detecting a mismatching region in accordance with the present invention, the region on the supporting material, to which region the mismatch polynucleotide was bound, is capable of being specified and detected in accordance with the results of the comparison. Accordingly, for example, data obtained from the thus detected region is capable of being eliminated from data analysis. As a result, background noise due to the mismatch binding is capable of being suppressed, and the detection accuracy is capable of being enhanced.

Also, with respect to the oligonucleotide probe having been fixed to the region on the supporting material, to which region the mismatch polynucleotide was bound, there is possibility that a polymorph, which slightly varies in base sequence, e.g. a single base polymorph (SNP) in the cases of a gene, will be contained in the polynucleotide having been used as the target. Therefore, in cases where the region on the supporting material, to which region the mismatch polynucleotide was bound, is capable of being specified, an analysis is capable of being performed even further with respect to the oligonucleotide probe of the region having been specified, and the SNP, or the like, is thus capable of being detected. Further, detection of specific gene deletion becomes possible, depending upon the selection of the oligonucleotide probes to be fixed to the supporting material.

DESCRIPTION OF THE PREFERRED EMBODIMENTS

The present invention will hereinbelow be described in further detail with reference to the accompanying drawings.

An embodiment of the method of detecting a mismatching region in accordance with the present invention, wherein a DNA array comprising a supporting material and a plurality of oligo DNA probes having been fixed respectively to a plurality of regions on the supporting material is utilized, will be described hereinbelow. FIGS. 1A to 1E are explanatory views showing how a mismatching region is detected with an embodiment of the method of detecting a mismatching region in accordance with the present invention.

Firstly, a surface of a membrane filter 1 acting as a supporting material is processed such that carboxyl groups (COOH) or aldehyde groups (COH) are exposed from the surface of the membrane filter 1 to the exterior. Also, an amino group (NH2) is introduced into a 5'-terminal of each of synthetic oligo DNA's acting as DNA probes 2, 2, . . . Each of the DNA probes 2, 2, . . . having the terminals, to which the amino groups have been introduced, is spotted onto the membrane filter 1, which has been subjected to the surface processing. As a result, a covalent bond is formed between the carboxyl group or the aldehyde group, which is exposed on the surface of the membrane filter 1, and the amino group, which has been introduced into the terminal of each of the DNA probes 2, 2, . . . In this manner, as illustrated in FIG. 1A, the DNA probes 2, 2, . . . are fixed to the membrane filter 1.

Figure 1A:
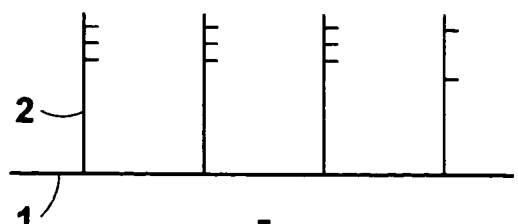
FIGS. 1A to 1E are explanatory views showing how a mismatching region is detected with an embodiment of the method of detecting a mismatching region in accordance with the present invention.

In FIG. 1A, part of each of the DNA probes 2, 2, . . . , which part extends vertically from the membrane filter 1, represents a sequence of the DNA. Also, each of parts, which branch out from the vertically extending part of each of the DNA probes 2, 2, . . . , represents the part, which complementarily forms a base pair. The DNA probes 2, 2, . . . having different sequences are respectively spotted onto regions of the membrane filter 1. The DNA probes 2, 2, . . . are prepared such that the DNA lengths are approximately identical with one another at all of the regions of the membrane filter 1. In FIG. 1A, as an aid in facilitating the explanation, one DNA probe 2 is fixed to one region (i.e., one spot) on the membrane filter 1. In this manner, only one DNA probe 2 may be fixed to each of the regions of the membrane filter 1. Alternatively, several DNA probes may be fixed to each of the regions of the membrane filter 1. Also, the DNA probes 2, 2, . . . may be the synthesized oligo DNA's. Alternatively, the DNA probes 2, 2, . . . may be the cDNA's having been isolated from cells of organisms.

Thereafter, a labeled DNA acting as a target is prepared. As the DNA of the labeled DNA, a total RNA, a poly-A+ RNA, or the like, which has been extracted from a cell or a tissue of an organism and purified, is subjected to reverse transcription using a reverse transcriptase, and a cDNA is thereby prepared. The labeled DNA may be prepared by incorporating a labeling substance into the cDNA during the reverse transcription using the reverse transcriptase. Also, biotin or DNP (dinitrophenyl) maybe incorporated into the cDNA during the reverse transcription, such that a signal may be amplified via an antibody reaction or an enzyme reaction.

The labeling substance may be selected from various labeling substances, for which the regularity of incorporation into the cDNA is known previously. By way of example, the labeling substance may be a fluoro chrome, such as Cy3, Cy5, or fluorescein isothiocyanate. Alternatively, the labeling substance may be a radioactive isotope, such as 32P or 33P. As another alternative, the labeling substance may be a labeling substance for chemical luminescence, such as alkaline phosphatase, peroxidase, luciferase, biotin, or digoxigenin.

Thereafter, a labeled DNA 3 is subjected to hybridization reaction with the DNA probes 2, 2, . . . , which have been fixed to the membrane filter 1. By way of example, the hybridization reaction may be performed with a process, wherein the membrane filter 1, to which the DNA probes 2, 2, . . . have been fixed, and a reaction liquid containing the labeled DNA 3 are put into a hybridization bag, vibrations are given to the hybridization bag, and the labeled DNA 3 is thereby moved through convection or diffusion in the hybridization bag. Alternatively, the hybridization reaction may be performed with a process utilizing a reactor provided with a pump, a syringe, or the like, in which the reaction liquid containing the labeled DNA 3 is capable of being forcibly caused to flow across each of the regions of the membrane filter 1.

After the hybridization reaction has been performed, such that the surplus labeled DNA, which has not been bound to the DNA probes 2, 2, . . . through the hybridization, may be removed, a washing liquid may be introduced into the hybridization bag or the reactor in order to wash the membrane filter 1.

Figure 1B:
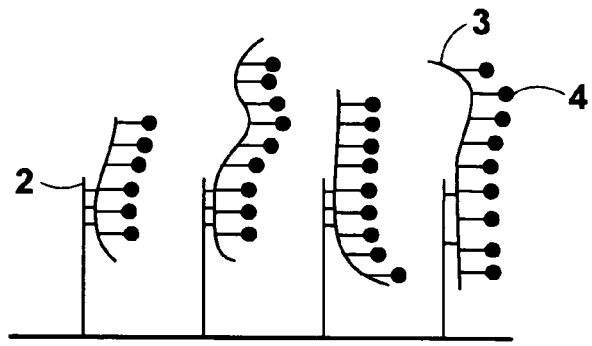

As illustrated in FIG. 1B, after the hybridization reaction has been performed, the labeled DNA 3, which has been labeled with a labeling substance 4 and has one of various different lengths, complementarily forms the base pair through the hydrogen bond with each of the DNA probes 2, 2, . . . (The DNA probe 2 and the labeled DNA 3 illustrated on the right end side of FIG. 1B are in a state in which they have moieties having not undergone a perfect complementary binding.) If the labeling substance 4 is detected in the state in which the labeled DNA 3 has one of various different lengths in the manner described above, a difference in signal intensity, which difference is obtained from a comparison between first detection data and second detection data described later, is not capable of furnishing an accurate index for specifying a region of the membrane filter 1, at which region a mismatch binding has occurred. Specifically, such that the difference in signal intensity, which difference is obtained from the comparison between the first detection data and the second detection data described later, is capable of furnishing an accurate index for specifying the region of the membrane filter 1, at which region the mismatch binding has occurred, it is necessary for the lengths of the labeled DNA 3 having been bound to the DNA probes 2, 2, . . . to be set at approximately identical lengths.

Therefore, in this embodiment, by use of exonuclease VII, a single-stranded moiety of the labeled DNA 3, which moiety has failed to form a double strand with each of the DNA probes 2, 2, . . . , is separated from the double strand, which has been formed by the labeled DNA 3 and each of the DNA probes 2, 2, . . . Exonuclease VII is a restriction enzyme capable of specifically acting upon a terminal of a single-stranded DNA and decomposing the single-stranded polynucleotide. In cases where the labeled DNA 3 having been bound to each of the DNA probes 2, 2, . . . is processed with exonuclease VII at a temperature falling within the range of 5oC to 20oC, as illustrated in FIG. 1C, the single-stranded moiety of the labeled DNA 3, which moiety has failed to form a double strand with each of the DNA probes 2, 2, . . . , is separated from the double strand, which has been formed by the labeled DNA 3 and each of the DNA probes 2, 2, . . . , and only the moieties, at which the labeled DNA 3 and each of the DNA probes 2, 2, . . . have formed the double strands, remain at each of the regions of the membrane filter 1.

Figure 1C:
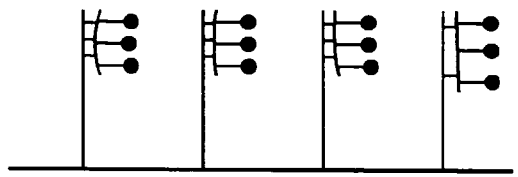

In the state illustrated in FIG. 1C, a first detection of the labeled DNA 3 is performed. The operation for the first detection varies in accordance with the kind of the labeling substance 4 with which the labeled DNA 3 has been labeled. For example, in cases where the labeling substance 4 is a fluoro chrome, excitation light is irradiated to the regions of the membrane filter 1, and the fluorescent labeling substance, which is contained selectively in the regions of the membrane filter 1, is excited by the excitation light to produce fluorescence. The thus produced fluorescence is detected photoelectrically by use of a CCD camera, a laser+ a PMT, or the like.

In cases where the labeling substance 4 is a radioactive isotope, a stimulable phosphor layer of a stimulable phosphor sheet is exposed to radiation radiated out from the radioactive labeling substance, which is contained selectively in the regions of the membrane filter 1. Thereafter, the stimulable phosphor layer is exposed to stimulating rays, which cause the stimulable phosphor layer to emit light in proportion to the amount of energy stored on the stimulable phosphor layer during the exposure of the stimulable phosphor layer to the radiation. The light emitted by the stimulable phosphor layer is detected photoelectrically.

In cases where the labeling substance 4 is a chemical luminescent labeling substance, such as an enzyme, which is capable of producing the chemical luminescence when being brought into contact with a chemical luminescence substrate, the chemical luminescent labeling substance, which is contained selectively in the regions of the membrane filter 1, is brought into contact with the chemical luminescence substrate. Also, the chemical luminescence produced by the chemical luminescent labeling substance is detected photoelectrically.

The detection data having been obtained with the first detection from each of the regions of the membrane filter 1 in the manner described above is taken as the first detection data.

Figure 1D:
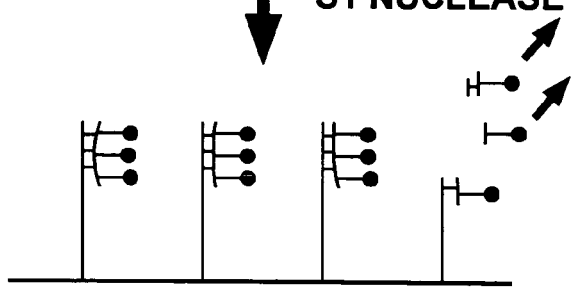

Thereafter, as in the cases of the moiety of the labeled DNA 3 illustrated on the right end side of FIG. 1D, the moiety of the labeled DNA 3, which has not formed a perfect base pair with the DNA probe 2 and is bound to the DNA probe 2 through a mismatch binding, is decomposed by use of S1 nuclease. S1 nuclease is one of nucleases purified from a filamentous fungus (Aspergillus oryzae). S1 nuclease is a restriction enzyme capable of decomposing a single-stranded RNA or a single-stranded DNA into a 5'-mononucleotide. With the action of S1 nuclease, a single-stranded moiety, at which a base pair has not been formed, is capable of being decomposed. In cases where the processing with S1 nuclease is performed at a temperature falling within the range of 5oC to 15oC, the moiety having undergone the mismatch binding as illustrated on the right end side of FIG. 1D is decomposed. As a result, as illustrated in FIG. 1E, the single-stranded moiety, at which the base pair was not formed, is removed.

Figure 1E:
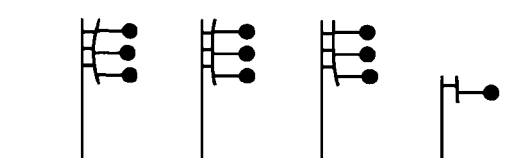

In the state illustrated in FIG. 1E, a second detection of the labeled DNA 3 is performed with the same detecting operation as that for obtaining the first detection data. The detection data having been obtained with the second detection from each of the regions of the membrane filter 1 in the manner described above is taken as the second detection data.

In the region of the membrane filter 1, at which region the labeled DNA 3 was bound through the mismatch binding, the single-stranded moiety, at which the base pair was not formed, has been decomposed by the action of S1 nuclease. Therefore, the second detection data obtained from the region described above represents a signal intensity obtained from the labeling substance 4, which signal intensity is markedly lower than the signal intensity represented by the first detection data corresponding to the region described above. Accordingly, in accordance with the results of the comparison made between the first detection data and the second detection data, the region of the membrane filter 1, at which region the labeled DNA 3 was bound through the mismatch binding, is capable of being specified and detected.

As described above, with this embodiment, after the labeled DNA 3 has been subjected to the hybridization with the DNA probes 2, 2, . . . , the single-stranded moiety of the labeled DNA 3, which moiety has failed to form the double strand with each of the DNA probes 2, 2, . . . , is separated from the double strand, which has been formed by the labeled DNA 3 and each of the DNA probes 2, 2, . . . by the action of exonuclease VII. Thereafter, the signal, which is obtained from the labeling substance 4 of the labeled DNA 3, is detected with respect to each of the regions on the membrane filter 1, and the first detection data is obtained from the signal detection. After the first detection data has been obtained, the second restriction enzyme is caused to act upon the mismatching moiety, at which the labeled DNA 3 and the certain DNA probe 2 among the DNA probes 2, 2, . . . have undergone the mismatch binding with each other. The second restriction enzyme is capable of cutting off the mismatching moiety. The mismatching moiety, at which the labeled DNA 3 and the certain DNA probe 2 have undergone the mismatch binding with each other, is thereby separated from the region on the membrane filter 1, to which region the mismatch DNA has been bound. Thereafter, the signal, which is obtained from the labeling substance 4 of the labeled DNA 3, is detected with respect to each of the regions on the membrane filter 1, and the second detection data is obtained from the signal detection. The first detection data and the second detection data are then compared with each other. Therefore, the region on the membrane filter 1, to which region the mismatch DNA was bound, is capable of being specified and detected in accordance with the results of the comparison. Accordingly, for example, at the time of the data analysis, the data obtained from the thus detected mismatching region is capable of being eliminated from the data analysis. As a result, background noise due to the mismatch binding is capable of being suppressed, and the detection accuracy is capable of being enhanced.

Also, it is capable of being found that the region, at which the signal intensity represented by the second detection data is markedly lower than the signal intensity represented by the first detection data, is the region, at which the single-stranded moiety having failed to form the base pair and having been separated by the action of S1 nuclease was present. Therefore, an analysis is capable of being performed even further with respect to the DNA probe 2 of the region having been specified, and the SNP, or the like, is thus capable of being detected. Further, detection of specific gene deletion becomes possible, depending upon the selection of the kinds of the DNA probes 2, 2, . . . to be fixed to the membrane filter 1.

In the embodiment described above, the DNA probes 2, 2, . . . are employed as the oligonucleotide probes. Also, the labeled DNA 3 is employed as the labeled polynucleotide. However, the method of detecting a mismatching region in accordance with the present invention is not limited to the use of the DNA probes 2, 2, . . . and the labeled DNA 3. For example, RNA's, nucleic acid precursors, or coenzymes may be employed in the method of detecting a mismatching region in accordance with the present invention.

What is claimed is:

1. A method of detecting a mismatching region, comprising the steps of:
   i) subjecting a labeled polynucleotide, which has been labeled with a labeling substance, to hybridization with a plurality of oligonucleotide probes, wherein said oligonucleotide probes have been fixed respectively to a plurality of regions on a supporting material,
   ii) causing a first enzyme to act upon a single-stranded moiety of the labeled polynucleotide, which moiety has failed to form a double strand with each of the plurality of the oligonucleotide probes having been respectively fixed to the plurality of the regions on the supporting material, wherein the first enzyme decomposes a single-stranded polynucleotide from a terminal of the labeled polynucleotide, the single-stranded moiety of the labeled polynucleotide being thereby separated from a double strand, which has been formed by the labeled polynucleotide and each of the oligonucleotide probes,
   iii) detecting a signal, which is obtained from the labeling substance of the labeled polynucleotide, with respect to each of the regions on the supporting material after the single-stranded moiety of the labeled polynucleotide has been separated from the double strand, which has been formed by the labeled polynucleotide and each of the oligonucleotide probes, first detection data being obtained from the signal detection,
   iv) causing a second enzyme to act upon a mismatching moiety, at which the labeled polynucleotide and a certain oligonucleotide probe among the plurality of the oligonucleotide probes having been respectively fixed to the plurality of the regions on the supporting material have undergone a mismatch binding with each other, after the first detection data has been obtained, wherein the second enzyme cuts off the mismatching moiety, at which the labeled polynucleotide and the certain oligonucleotide probe have undergone the mismatch binding with each other, being thereby separated from a region on the supporting material, to which region the mismatch polynucleotide has been bound,
   v) detecting a signal, which is obtained from the labeling substance of the labeled polynucleotide, with respect to each of the regions on the supporting material after the mismatching moiety has been separated from the region on the supporting material, to which region the certain oligonucleotide probe has been fixed, second detection data being obtained from the signal detection,
   vi) making a comparison between the first detection data and the second detection data, and
   vii) specifying the region on the supporting material, to which region the mismatch polynucleotide was bound, in accordance with results of the comparison, thereby detecting a mismatching region.

2. The method as defined in claim 1 wherein the first enzyme is exonuclease VII.

3. The method as defined in claim 1 wherein the second enzyme is at least either one of S1 nuclease and mung bean nuclease.

4. The method as defined in claim 2 wherein the second enzyme is at least either one of S1 nuclease and mung bean nuclease.

5. The method as defined in claim 1 wherein the labeling substance is selected from the group consisting of a radioactive labeling substance, a fluorescent labeling substance, and a chemical luminescent labeling substance that produces a chemical luminescence when being brought into contact with a chemical luminescence substrate.

* * * * *